United States Patent [19]

Klemm

[11] Patent Number: Plant 5,288

[45] Date of Patent: Oct. 2, 1984

[54] CARNATION NAMED KLEMGORI

[76] Inventor: Siegfried Klemm, Hanfacker 9, 7000 Stuttgart 50, Fed. Rep. of Germany

[21] Appl. No.: 402,064

[22] Filed: Jul. 26, 1982

[51] Int. Cl. ..... A01H 5/00
[52] U.S. Cl. ..... Plt./70
[58] Field of Search ..... Plt./70

*Primary Examiner*—James R. Feyrer
*Attorney, Agent, or Firm*—Charles W. Rummler

[57] ABSTRACT

A new variety of carnation plant distinguished by the very light green-yellow coloring of its medium sized blooms which are borne on sturdy pedicels carried by long, strong peduncles and by its continuous and profuse production of flowers.

1 Drawing Figure

BACKGROUND OF THE NEW PLANT

This new carnation cultivar originated at Stuttgart, West Germany, as a sport of an unpatented carnation variety named "Ministar" being grown in my greenhouses for the production of cut flowers, as well as for propagation and sale of plants to commercial growers for spray carnation uses. This sport was discovered by me in my greenhouses at Stuttgart on Dec. 2, 1975, and was selected for propagation because of its bright, very pale yellow coloration. Propagation of this plant through successive generations by means of cuttings has demonstrated that the new plant has not only retained the continuous and abundant production capability of its parent but also that its distinguishing characteristics hold true from generation to generation and appear to be firmly fixed.

DESCRIPTION OF THE DRAWING

My new carnation cultivar is illustrated by the accompanying full color photographic drawing, which shows the inflorescense of a fully grown plant, the view including buds in various stages of opening, as well as fully opened flowers.

DESCRIPTION OF THE NEW PLANT

The following is a detailed description of my new carnation cultivar based upon observation of plants grown under conventional greenhouse procedures, the color designations being according to The R.H.S. Colour Chart published by The Royal Horticultural Society of London, England.

THE PLANT

Origin: Sport.
Parentage: Ministar (unpatented).
Classification:
- *Botanic.*—Dianthus Caryophyllus.
- *Commercial.*—Spray carnation.

Form: Bush.
Height: About 90 cm. to about 120 cm.
Growth: Vigorous and upright with good strength.
Branching: Normal.
Foliage:
- *Quantity.*—Moderate.
- *Leaf Size.*—Moderate.
- *Shape.*—Oblong with entire margins.
- *Texture.*—Smooth.

- *Color.*—Upper side — Blue-Green. Under side — Blue-Green.

THE BUD

Size: Medium, about 15 mm. in diameter and about 40 mm. long.
Form: Generally ovoid, becoming cylindrical when opening.
Opening rate: Moderate.
Color:
- *When sepals first divide.*—Greenish-Yellow.
- *When petals begin to unfurl.*—Greenish-Yellow.

Sepals:
- *Condition.*—Upstanding.
- *Color.*—Inside — Grey-Green. Outside — Yellow-Green.

Calyx:
- *Shape.*—Cylindrical.
- *Size.*—Moderate, about 15 mm. broad and about 17 mm. long.
- *Splitting.*—The calyx does not split.
- *Aspect.*—Smooth.

Peduncle: Rigid and erect.
- *Color.*—Grey-Green.

THE FLOWER

Blooming habit: Continuous and profuse.
Size of bloom: Medium.
- *Diameter.*—About 60 to 65 mm.
- *Depth.*—About 30 to 35 mm.

Borne: Singly on strong, upright pedicels.
Shape: High centered when bloom opens and this shape does not change.
Petalage:
- *Number of petals.*—About 34.
- *Arrangement.*—Generally imbricated.
- *Shape of petals.*—Fan-shaped with toothed margin.
- *Color.*—Outer and inside petals — R.H.S. 2C-3D with fine red stripes about 15 mm. long and 1 mm. broad extending lengthwise from tips of petal ruffles. Reverse side — R.H.S. 2C-3D.
- *Texture.*—Soft.
- *Appearance.*—Shiny.

Peduncle: Flowering stem — Sturdy and upright.
- *Length.*—About 45 cm.
- *Color.*—Grey-Green.
- *Persistence.*—The petals hang on and dry and the bloom stays upright.

Fragrance: None.

Lasting quality:

*On plant.*—About 16 days.

*As a cut flower.*—About 12 days.

REPRODUCTIVE ORGANS

Stamens: Anthers and pollen are rarely present.

Pistils: Not more than three.

*Length.*—About 40 mm.

*Stigmas.*—Color — Cream Yellow.

Fruit: Fertile.

*Shape.*—Cylindrical.

*Color.*—Green/Brown at maturity.

I claim:

1. A new and distinct carnation cultivar, substantially as herein shown and described, characterized by its high productivity of bright yellow flowers borne singly on rigid, erect pedicels carried in spray formation on a sturdy and upright peduncle.

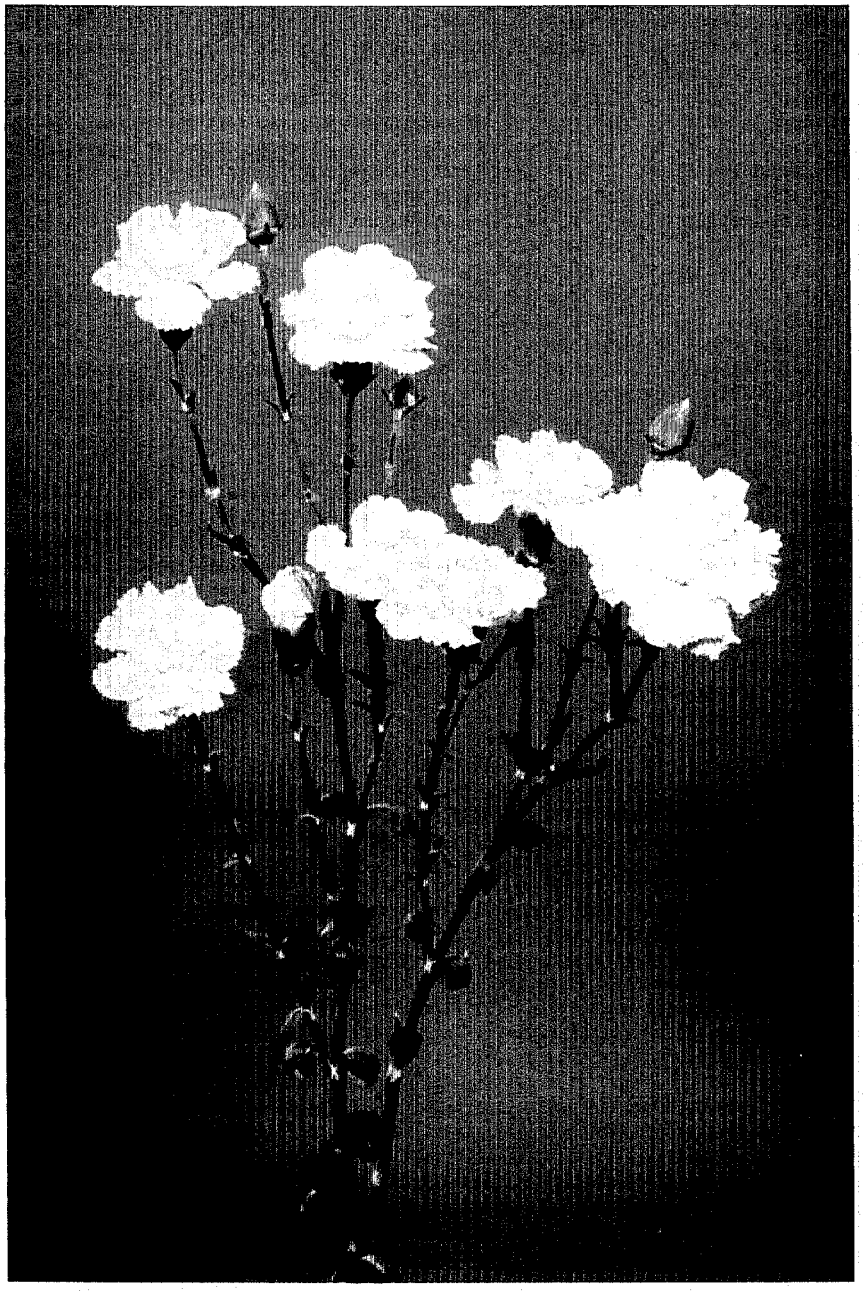

* * * * *